United States Patent
Venkat et al.

(10) Patent No.: US 10,741,272 B2
(45) Date of Patent: Aug. 11, 2020

(54) TERM CLASSIFICATION BASED ON COMBINED CROSSMAP

(71) Applicant: CERNER INNOVATION, INC., Kansas City, KS (US)

(72) Inventors: Savitha Venkat, Leawood, KS (US); Thomas C. Gifford, Kansas City, MO (US); Christopher S. Finn, Liberty, MO (US); Margaret C. Kolm, Kansas City, MO (US); Chad A. Cole, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 793 days.

(21) Appl. No.: 14/521,557

(22) Filed: Oct. 23, 2014

(65) Prior Publication Data
US 2016/0117445 A1    Apr. 28, 2016

(51) Int. Cl.
*G16H 10/60* (2018.01)
*G06F 19/00* (2018.01)

(52) U.S. Cl.
CPC .......... *G16H 10/60* (2018.01); *G06F 19/324* (2013.01)

(58) Field of Classification Search
CPC .... G16H 10/60; G06F 19/324; G06F 19/3406
See application file for complete search history.

(56) References Cited

U.S. PATENT DOCUMENTS

| 8,346,804 B2 * | 1/2013 | Phillips | G06Q 10/06 707/780 |
| 2010/0318549 A1 * | 12/2010 | Mayr | G06F 19/322 707/759 |

OTHER PUBLICATIONS

Lee, Lau; "Exploratory Reverse Mapping of ICD-10-CA to SNOMED CT"; Proceedings of the 3rd international conference on Knowledge Representation in Medicine (KR-MED 2008).*

* cited by examiner

*Primary Examiner* — Linh Giang Le
(74) *Attorney, Agent, or Firm* — Shook, Hardy & Bacon L.L.P.

(57) ABSTRACT

Methods, systems, and computer storage media are provided for converting a source in a first terminology to a target in a different terminology. A source in a first terminology may be converted to a target in a second terminology using cross maps that map sources to all possible matching targets, probability data derived from frequency data illustrating a frequency of selection for targets in relation to specific sources, lexical matching algorithms indicating targets with highest lexical matches for specific sources, or a combination thereof. Any one, or a combination, of the data above may be used to identify a probabilistically most relevant target in a desired terminology.

20 Claims, 4 Drawing Sheets

TERM CLASSIFICATION BASED ON COMBINED CROSSMAP

BACKGROUND

Many different medical terminologies are currently in use today. A different terminology may be used among different institutions to describe the same type of service. With the use of so many terminologies to describe the same things, there exists an increased likelihood of confusion when reviewing data in multiple terminologies. A single vocabulary has yet to be agreed upon by all institutions, in particular, healthcare institutions. The use of many different medical terminologies requires efficient conversion of medical terms, phrases, codes, etc. from one medical terminology/vocabulary to another medical terminology/vocabulary. Manual conversions from one medical terminology/vocabulary to another are incredibly slow, inefficient, and expensive. Furthermore, manual conversions simply map one terminology/language to any possible matches in another terminology. For instance, a term in a first terminology may correspond to 57 terms in a second terminology. For obvious reasons, the term in the first terminology should not be converted to each of the 57 targets. Thus, a specific, best match, is not identified based on existing data.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-readable media for converting terms in a first terminology to target terms in a different terminology. In embodiments, the terms converted are medical codes but the invention is not limited in this regard. A source term in a first terminology may be converted to a target term in a second terminology using available information such as cross maps that map source terms to all possible matching target terms, probability data derived from frequency data illustrating a frequency of selection for target terms in relation to specific source terms, lexical matching algorithms indicating target terms with highest lexical matches for specific source terms, or a combination thereof. Any one, or a combination, of the information may be used to identify a probabilistically most relevant target term in a desired terminology.

BRIEF DESCRIPTION OF THE DRAWINGS

Embodiments are described in detail below with reference to the attached drawings figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for converting terms in a first terminology to target terms in a different terminology. In embodiments, the terms converted are medical codes but the invention is not limited in this regard. A source term in a first terminology may be converted to a target term in a second terminology using cross maps that map source terms to all possible matching target terms, probability data derived from frequency data illustrating a frequency of selection for target terms in relation to specific source terms, lexical matching algorithms indicating target terms with highest lexical matches for specific source terms, or a combination thereof. Any one, or a combination, of the data above may be used to identify a probabilistically most relevant target term in a desired terminology.

Many advantages will become apparent, but to name a few, embodiments enable a best match to be automatically identified. This saves time, money, etc. and reduces the likelihood of error associated with working with many terminologies.

A first aspect is directed to a computerized method, carried out by at least one server having one or more processors, of converting terms. The claim recites identifying a source element in a source terminology for a patient, wherein the source element includes a numerical medical code and a text associated therewith. The text may be free text or text selected from a menu. The source element is mapped to one or more target elements in a target terminology, where the target terminology is different from the source terminology. It is determined, using the text associated with the source element, that a first target element in the target terminology of the one or more target elements is a match to the source element in the source terminology based on a lexical match of the text associated with the source element and a lexical description of the first target element. The source element in the source terminology is converted to the target element in the target terminology.

A second aspect is directed to a system for converting terms. The system includes a conversion engine having one or more processors and one or more computer storage media; and a data store coupled to the conversion engine, wherein the conversion engine identifies a source element to be converted to a target element, each of the source element and the target element being associated with different terminologies; and determines a match of the target element to the source element based on a probability derived from a frequency of selection indication of the target element when mapping the source element.

A third aspect is directed to one or more computer-readable media having computer-executable instructions embodied thereon that, when executed, facilitate a method of converting terms. The method includes identifying a source element in a source terminology to be converted to a target terminology. The target terminology may be Systemized Nomenclature of Medicine—Clinical Terms®, and wherein the source element includes a numerical medical code and text associated therewith; determining whether the text associated with the source element is an exact match with any lexical descriptions of one or more target elements of the target terminology; upon determining there is not an exact match, determining whether there is a crossmap of the source element to a subset of target elements corresponding to the source element; upon determining there is a crossmap, identifying a first target element of the subset of target elements to associate with the source element based on (1) a probability derived from a frequency of selection indication of the first target element for mapping to the source element and (2) a lexical match of the text associated with the source element and a first lexical description of the first target element; and converting the source element to the target element.

Figure 1:
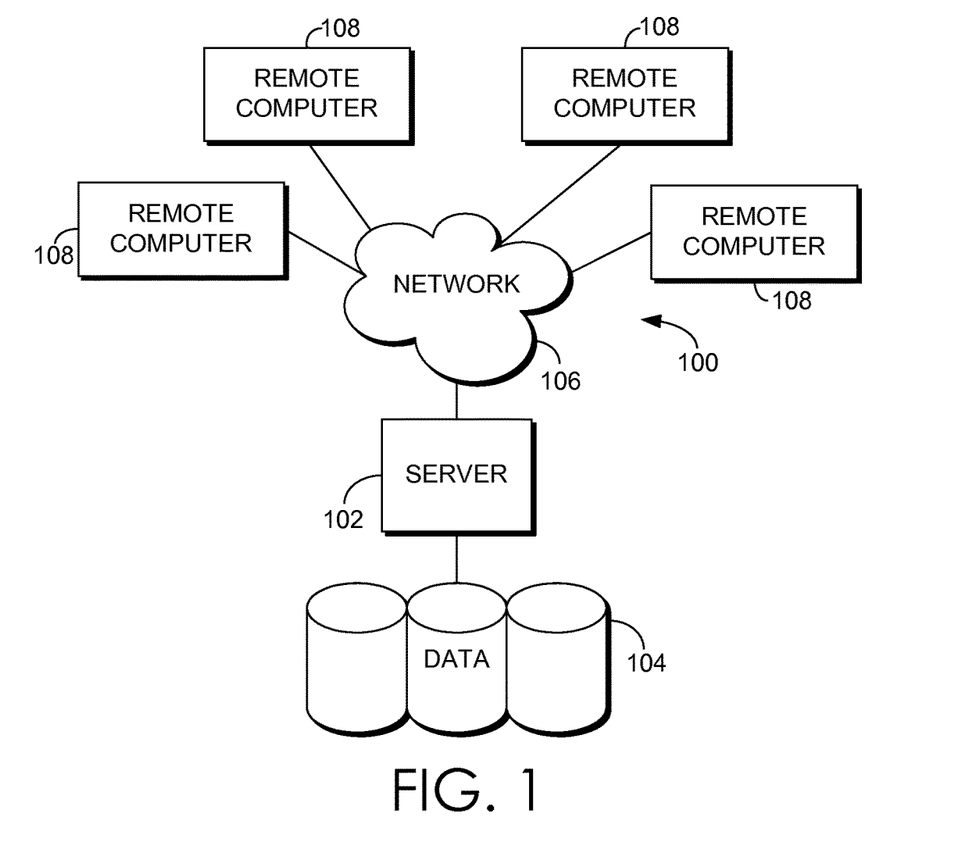
FIG. 1 is a block diagram of an exemplary computing system suitable to implement embodiments of the present invention.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer-readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health-care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

As previously mentioned, the present invention is directed to converting a source in a first terminology to a target in a different terminology. In embodiments, the items converted are medical codes but the invention is not limited in this regard. For example, a first medical code in a first terminology, ICD-9 for instance, may be mapped to a plurality of medical codes in a second terminology such as SNOMED CT®. A source in a first terminology may be converted to a target in a second terminology using cross maps that map sources to all possible matching targets, probability data derived from frequency data illustrating a frequency of selection for targets in relation to specific sources, lexical matching algorithms indicating targets with highest lexical matches for specific source terms, or a combination thereof. Any one, or a combination, of the data above may be used to identify a probabilistically most relevant target in a desired terminology. Additionally, semantic match may also be utilized in the present invention. For example, entry of HTN represents hypertension but the two terms are not keyword or lexical matches. Conceptually, however, they are the same. A semantic match may identify hypertension as a match for HTN where a lexical match may not. Any known method of identifying semantic matches may be utilized.

Figure 2:
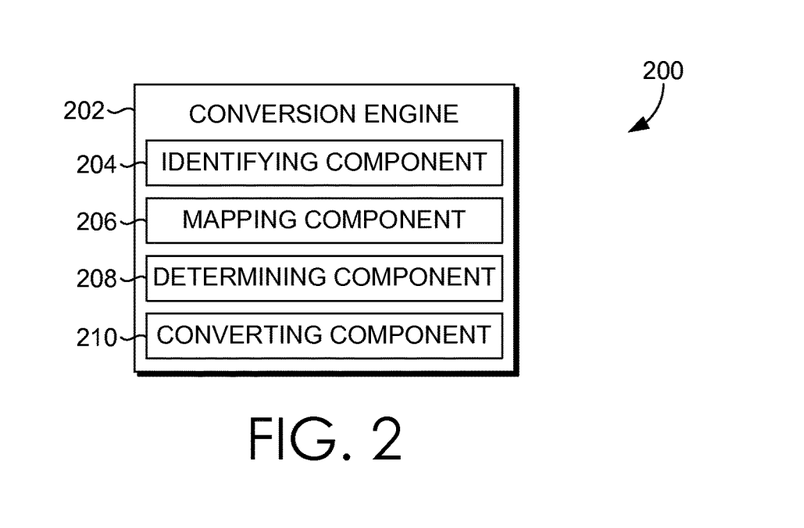
FIG. 2 depicts an exemplary computing environment suitable for implementing embodiments of the present invention.

Turning now to FIG. 2, an exemplary computing environment 200 suitable for implementing embodiments of the present invention is illustrated. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Among other components not shown, the environment 200 may include a conversion engine 202. The conversion engine 202 may be embodied on any computing device such as a personal computer, laptop device, mobile phone, or any computing device suitable for use with the present invention. The conversion engine may also be embodied on, for example, a remote server of a distributed computing environment. In embodiments of the invention that are practiced in distributed computing environments, communication is linked through appropriate connections. These connections may be wired or wireless. Examples of particular wired embodiments, within the scope of the present invention, include USB connections and cable connections. Examples of particular wireless embodiments include networks including, without limitation, one or more local area networks (LANs) and/or wide area networks (WANs). Such networking environments are commonplace in offices, enterprise-wide computer networks, intranets and the Internet. Accordingly, the network environment is not further described herein.

It will be understood and appreciated by those of ordinary skill in the art that the exemplary environment 200 shown in FIG. 2 is merely an example of one suitable computing environment and is not intended to suggest any limitation as to the scope of use or functionality of the present invention. Neither should the exemplary environment 200 be interpreted as having any dependency or requirement to any single component or combination of components illustrated therein.

The conversion engine 202 may be configured for, among other things, facilitating conversion of a source in one terminology to a target in another terminology. The conversion engine 202 may include, among other components, an identifying component 204, a mapping component 206, a determining component 208, and a converting component 210.

The identifying component 204 may be configured for, among other things, identifying a source. A source, as used herein, refers generally to an item in a first terminology desired to be converted to a target in a different terminology. In embodiments, a source and a target are medical codes in a first and second terminology, respectively. In embodiments, the second terminology is SNOMED CT®. In embodiments where the source and target are medical codes, each is associated with a numerical medical code value (which may be different from one another) and the source is associated with text and the target is associated with a textual lexical description. These may be referred to as source elements or source medical codes, each being interchangeable and both terms may include both a numerical medical code value and a textual description of the numerical medical code.

A source may be identified in a patient's electronic health record (EHR) or any other location where information to be converted may be stored. The source may be identified as it is entered into, for example, the patient's EHR. Alternatively, the source may be identified subsequent to entry. For instance, sources may be entered into a patient's EHR prior to a predetermined time period. Such sources may be referred to as historical sources. Such entries exist, for instance, when a source has been documented in a patient's EHR at, for example, a previous visit. Thus, historical sources are sources that were documented prior to a present documentation session. Additional data sources including information to convert may include personal health records, health information exchanges (HIEs), population health records, consumer-reported information, HIE-imported sources of nomenclature, etc.

The mapping component 206 may be configured for, among other things, mapping one or more sources to a terminology associated with one or more targets. Mapping, as used herein, refers generally to identifying one or more targets that are associated with one or more sources in a crossmap. A crossmap is a compilation of one or more mappings of sources to targets where a term or concept from a source is linked to a term or concept in a target, both the source and target being in different terminologies. Crossmaps may be proprietary, released by organizations such as the government, and the like. Crossmaps may include a plurality of targets linked to a source such that there are numerous possible matches for a source. In embodiments, the crossmaps utilized are predefined mappings already in existence. However, it could be contemplated that, in situations where crossmaps do not exist, the mapping component 206 may be configured to generate a newly created crossmap.

In an embodiment, crossmaps include links for a source (e.g., source medical code) and one or more targets (e.g., target medical codes). For example, a source element may be input for a skin disorder '709.8—disorders of the skin' into a patient's EHR. The input may be in a first terminology such as, for example, ICD-9 or ICD-10. If this element were desired to be converted to SNOMED CT®, there would be multiple matches along the order of 180 matches. The element input includes a numerical medical code value (i.e., 709.8). The input may also include a text. In this example, the text is 'disorders of the skin' but can be any text associated with the numerical value. Text may be free text, which is text that is manually input. For example, a clinician could input code 709.8 and manually input text as a description of 'skin disorder'. Alternatively, the text may be selected from one or more predetermined selection options associated with the numerical value. For example, when entering 709.8, one or more selection options associated with the numerical value may automatically populate such that a user can select from the pre-populated options. This textual description, along with the numerical value, may be included in the source element. The textual description may include both free text and text selected from a populated menu.

The determining component 208 may be configured for, among other things, determining a match of a source to a target. As described above, sources may be associated with a plurality of targets in a crossmap. The determining component 208 may identify an appropriate match using a textual description of the source, a lexical description of the target, a probability derived from a frequency of selection indication of the target with a given source, and the like. A lexical description of the target is similar to the textual description of the source (described above) in that it is a text string describing the target. For example, a target element of 1234.56 may be associated with a lexical description of 'diabetes mellitus type I' identifying the target element. A lexical match may be identified using a lexical match algorithm such as n-gram or Levenshtein algorithm or any other appropriate algorithm identified by those skilled in the art.

A probability derived from a frequency of selection indication of a target represents the probability that a target is a match based on how frequently a particular target is selected for a particular source. For example, a source may be an ICD-9 medical code of '250.00 Diabetes Mellitus'. Assume this input maps to 46 possible SNOMED CT® target codes. Each of the 46 possible matches may be associated with, among other things, a probability derived from a frequency of selection based on how often it is selected for the source '250.00—diabetes mellitus'. The data indicating a frequency of selection may be institution-specific such that the data regarding the frequency indicates how often the target is selected within a particular institution. This may be particularly valuable since institutions in different geographical locations inherently see different clinical conditions. For instance, a source of 709.8—skin disorders for a general clinical may be commonly mapped to a target of 'rash' while the same source input into a burn facility may be mapped to 'burn' more frequently than any other target.

The determining component 208 may use each of the above described data independently to identify a target match or a combination thereof. In embodiments, both a lexical match (i.e., comparing the text description of a source with a lexical description of a target) and a probability derived from a frequency of selection indication are used. In alternative embodiments, only the lexical data is utilized to identify a target match. Furthermore, the probability based on frequency of selection may be utilized independently to identify a target match. Weighting may be utilized when using the above methods to rank various types of data. For instance, exact lexical matches may be given higher weights since they are exact matches. The probability data may be weighted according to various rules as further described below.

The sources of data (e.g., a probability derived from a frequency of selection, lexical match, etc.) may be combined together using an algorithm to weigh each portion of data based on its relevancy and accuracy for a given terminology conversion (e.g., ICD-9 to SNOMED CT®) and a given provider (e.g., the institution). For example, assume that in a given database an ICD-9 code '453.40' was used 100 times. The below frequency data is an example of how often this case is mapped to an associated target code (in this case, a SNOMED CT® code) in a crossmap.

TABLE 1

| SNOMED CT® TEXT | Frequency | P(X/Y) | P(Z/X, Y) LEXICAL | P(Z/X, Y*) CONCEPTUAL | BAYES THEOREM [P(X/Y)] * [P(Z/X, Y)] | BAYES THEOREM [P(X/Y)] * [P(Z/X, Y*)] |
|---|---|---|---|---|---|---|
| Deep venous thrombosis | 40 | 0.4 | 0.001 | 0.9 | 0.0004 | 0.36 |
| Deep venous thrombosis of lower extremity | 20 | 0.2 | 0.001 | 0.01 | 0.0002 | 0.002 |
| Acute deep vein thrombosis of lower limb | 15 | 0.15 | 0.001 | 0.01 | 0.00015 | 0.0015 |
| Deep vein thrombosis of bilateral LE | 10 | 0.1 | 0.001 | 0.01 | 0.0001 | 0.001 |
| Deep vein thrombosis of leg related to air travel | 5 | 0.05 | 0.001 | 0.01 | 0.00005 | 0.0005 |
| Deep vein thrombosis of leg related to IV drug use | 3 | 0.03 | 0.001 | 0.01 | 0.00003 | 0.0003 |
| Thrombosis of vein of lower leg | 2 | 0.02 | 0.001 | 0.01 | 0.00002 | 0.0002 |
| All other possibilities (combined) | 5 | 0.05 | 0.993 | 0.04 | 0.04965 | 0.002 |
| SUM | 100 | 1 | 1 | 1 | NA | NA |
| Highest value term | | Deep venous thrombosis | none | Deep venous thrombosis | Deep venous thrombosis | Deep venous thrombosis |

A 'prior probability' may be calculated from the above frequency data as follows. The probability that the target code of 'deep venous thrombosis' was chosen in the past, given that the source was ICD-9 code 453.30, is 40/100 (total count)=0.40. The probability that the target code of 'deep venous thrombosis of lower extremity' was chosen in the past, given that the source code was ICD-9 453.30, is 20/100=0.20, etc. This prior probability, based on the frequency, is the P(X/Y) term in Bayes' Theorem as used below. This P(X/Y) term in Bayes' Theorem is independent of the X quantity that is maximized over, so it may be ignored. The P(Z/X,Y) term is calculated based on the lexical (or conceptual) similarity between text associated with the source (ICD-9 in this case) and target. Assume the source text in this example is "DVT". The lexical similarity between "DVT" and each of the cross-mapped text choices would not be high so a low probability (0.001) was assigned to each P(Z/X,Y) term. This probability may be calculated from some distance metric, such as the Jaccard distance.

Bayes' Thereom may be used to assign a quantitative value to each possible target and then take the maximum value of the possible targets within the cross map set, ψ. The cross map set lists all possible target terms for a given source term, including their relative probability based on frequency of prior use as indicated in the below equation:

$$\max_{X \in \varphi} P(X \mid Y, Z) = \max_{X \in \varphi} \frac{P(Z \mid X, Y) P(X \mid Y)}{P(Z \mid Y)} \quad \text{Equation 1}$$

where X represents a target (e.g., a SNOMED CT® term), Y refers to the source (e.g., an ICD-9 term), and Z refers to the text associated with the source. Put simply, P(X/Y,Z) means "The probability that a particular target is the best choice, given that a particular source and text pair was used for the input." The term P(Z/X,Y) may be calculated using an inverse distance score that is given by either a lexical matching algorithm, such as Levenshtein or n-gram, or a conceptual matching algorithm. The matching may be between the lexical description of the target and the text associated with the source. The probability for this value is highly irregular and changes for every X,Y pair. The P(Z/Y) term may be referred to as the 'prior' probability and may be evaluated based on a table of frequency of selection data of how past sources were matched to targets in historical data. The P(Z/Y) term may be the same for each element of ψ so it can be ignored since it does not affect maximization. Since P(Z/X,Y) may not be known exactly, approximations may be used. An exemplary approximation may be to identify the best lexical matches between Z and (X,Y) and convert their distances to a normalized probability from such that the sum is unity. Candidates with shorter distances (e.g., 0.0) (e.g., an exact lexical match) should have a much greater probability assigned to it than a candidate that has a distance of anything greater than 0.0.

The data in the above columns represent five different ways of combining methods to find a "best match". All five of the methods use a cross map to filter possible targets. Frequency data may be used to identify a final match or lexical data, or both. Conceptual similarity is another way to calculate P(Z/X,Y). The conceptual similarity between "DVT" and each of the choices is greater, although the first choice of "deep venous thrombosis" may be the best choice in this case so it was given a high probability at 0.9. Associating probabilities to conceptual matching between source and target terms may be achieved using method of Natural Language Processing (NLP). For this example, however, probabilities were manually chosen. The final two columns use Bayesian methods to combine both frequency and either lexical or conceptual analysis, to identify a match.

Although 'deep venous thrombosis' was found to be the best choice in each method except the pure lexical method, the strength of the match varies in each approach with the results from the last column giving the 'strongest match' due to the magnitude of the winning metric value (0.36) being much greater than the second largest value (0.002). This is due to the fact that two approaches—frequency and conceptual matching—were combined. Each method individually produces the same answer, but when combined, creates an even higher probability of identifying the best match.

Using the above methods, a conversion taking place at an institution with large quantities of accurate past patient records may weigh the frequency of selection data more heavily than a conversion that takes place at an institution having poor or sparse records on past frequency of selection data. In the latter case, a user may ignore the frequency of selection data entirely (e.g., weigh it as 0) or use a frequency of selection data table from a generic source (rather than an institution-specific table) and weigh the frequency data very low (below a predetermined threshold). Accuracy of frequency data may increase as data becomes specific to an institution. For example, the most accurate data may be for a specific department (e.g., Emergency Department) of an organization while the next accurate data may be for the entire organization. Additionally, data specific to a geographic region encompassing an institution would be more accurate than data aggregated across an entire country. The weight in the above-described algorithm assigned to the frequency depends on the relevance/accuracy. The combination of frequency data with other methods improves the probability of identifying a best match. Furthermore, in situations where frequency data may not be available, a standard frequency value may be utilized to improve calculations.

The converting component 210 may be configured for, among other things, converting the source in a source terminology to a target in the target terminology. The target subject of the conversion is the target identified by the determining component 208 as the target match. Once converted, the converted term may be stored in a database, in association with a patient's EHR, and the like. The converted term may replace the source in the patient's EHR or be stored in addition to the source in the patient's EHR.

Figure 3:
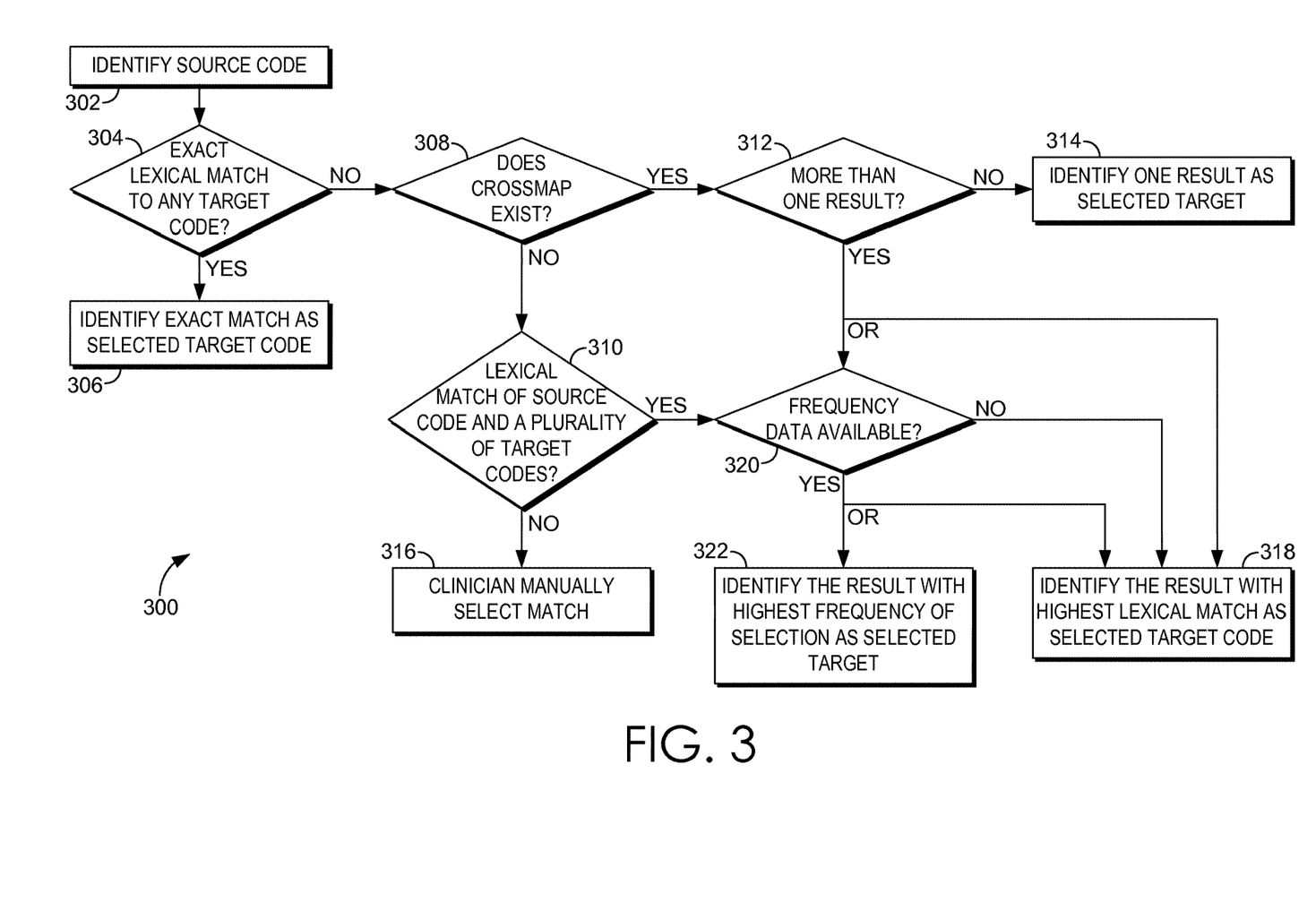
FIG. 3 depicts a flow diagram of a method for converting terms, in accordance with an embodiment of the present invention.

FIG. 3 provides an overview of the process 300. This particular example uses medical codes as the subject but the process 300 may be applied to any source converting to a different terminology. Initially, at block 302, a source code is identified. The source code may be identified as it is input in the EHR or from a previous visit as historical data. Initially, the process 300 may determine whether an exact lexical match to any target code exists at block 304. This matching is performed by comparing text associated with the source to lexical descriptions of target codes. The target codes may be any target code accessible as a filtering of the target codes available has not yet been performed. Thus, in the case of converting from ICD-9 to SNOMED CT®, this analysis could be performed on any SNOMED CT® target code. An exact lexical match is given the highest weight in the process 300 and, thus, if an exact lexical match is identified, the exact match is identified as the selected target code at block 306 and trumps any other potential matches. If an exact lexical match is determined to not exist at block 304, it is determined whether a crossmap exists at block 308. If a crossmap does not exist, the lexical description of a plurality of targets and the text associated with the source are evaluated for a lexical match at block 310 using the above-described algorithm. The plurality of targets may be any target available, as used in block 304, or it may be narrowed to a subset of targets specific to the source as much as possible without a crossmap. If there is no lexical match at block 310, a clinician may manually select a match at block 316. If there is a lexical match, then a determination of whether frequency data is available is made at block 320. Frequency data may include any type of frequency data including proprietary frequency data (custom to an institution) or non-proprietary frequency data (e.g., national data).

Upon determining a crossmap exists at block 308, it is determined whether there is more than one result (e.g., possible targets) in the crossmap at block 312. If there is only one result in the crossmap, the one result is identified as the selected target match at block 314. If, however, there is more than one result, a determination is made at block 320 of whether frequency data is available.

Upon determining frequency data is not available, the result with the highest lexical match is selected as the target match at block 318. If frequency data is available, the process may either identify the result with the highest lexical value as the target match at block 318 or identify the result with the highest frequency of selection as the selected target at block 322. Further, a target match may be identified using a combination of the frequency data and the lexical match. Additionally, when frequency data is not available it may still be combined with lexical match data by using a standard or default probability value for a combination calculation using the lexical match data and the standard probability value. This standard probability value may be estimated using, for example, data contributed from clients/users such that estimated probability values are available.

In application, assume a source code is entered as '453.40' which is an ICD-9 code. The text associated with the code in this example is "DVT" and it may be free text that was manually entered or it may be text automatically given in a pre-populated list of options. Initially, it would be determined if there is an exact match to the text "DVT" in the target dictionary. The target dictionary, in this example, may be a SNOMED CT® dictionary but could be any desired terminology. In this particular example, there is no exact match in the SNOMED CT® dictionary to the text "DVT" so a crossmap of ICD-9 to SNOMED CT® is referenced for the code '453.40'. In the crossmap, assume there are multiple possible target matches in the SNOMED CT® dictionary. The multiple possible target matches may be referred to as a subset of target matches since the entire dictionary has been filtered. An exemplary portion of a crossmap is illustrated below.

| SNOMED CT ® TERM CODE | SNOMED CT ® CONCEPT |
| --- | --- |
| Deep vein thrombosis | 128053003 |
| Deep venous thrombosis | 128053003 |
| DVT—deep vein thrombosis | 128053003 |
| Deep vein thrombosis of lower limb | 404223003 |
| Deep vein thrombosis of leg | 404223003 |
| Deep vein thrombosis of lower extremity | 404223003 |

Here, the SNOMED CT® term (or lexical description of the target) may be compared to the text associated with the source to identify a lexical match. There may not be a term lexically similar to the text DVT. In that case, frequency data or a probability based on frequency data may be utilized. An exemplary probability tab has been added to the below table.

| SNOMED CT® TERM | SNOMED CT® CONCEPT CODE | PROBA-BILITY |
|---|---|---|
| Deep venous thrombosis | 128053003 | 0.1021 |
| Deep venous thrombosis of lower extremity | 404223003 | 0.0373 |
| Acute deep vein thrombosis of lower limb | 651000119108 | |
| Deep vein thrombosis of bilateral LE | 444325005 | |
| Deep vein thrombosis of leg related to air travel | 134399007 | |
| Deep vein thrombosis of leg related to IV drug use | 413956008 | |
| Thrombosis of vein of lower leg | 234043001 | |

In this case, "deep venous thrombosis" with a value of 0.1021 is the most frequently selected associated with input of "DVT" and, as such, may be identified as the target match. The source "DVT" would then be converted to the SNOMED CT® code "128053003" and corresponding lexical description "deep venous thrombosis".

Another example is provided to illustrate an embodiment of the invention. Assume a source input is ICD-9 code 272.4 with associated text "hyperlipemia" that may have been free text or selected from a prepopulated list. Initially, evaluate the text for an exact match with a lexical description of a target in, for example, a target dictionary. There is no exact match for "hyperlipemia" in the SNOMED CT® dictionary. Next, it is determined that there is a crossmap available and the input is crossmapped to potential target matches. In an exemplary ICD-9-to-SNOMED CT® map, the ICD-9 code 272.4 maps to multiple SNOMED CT® target entries. Among the possible matches, the lexical similarity is evaluated to find a target match. An exemplary portion of a crossmap is provided below.

| SNOMED CT® TERM | SNOMED CT® CODE |
|---|---|
| Alpha/beta lipoproteinemia | 234413005 |
| Chemically induced hyperlipidemia | 426161002 |
| Diabetic dyslipidemia associated with type 2 diabetes mellitus | 761000119102 |
| Disorder of lipoprotein storage and metabolism | 238037008 |
| Dyslipidemia associated with type II diabetes mellitus | 761000119102 |
| Familial combined hyperlipidemia | 238040008 |
| Familial hyperlipoproteinemia type IIb | 238040008 |
| Familial multiple lipoprotein-type hyperlipidemia | 299465007 |
| FCHL—familial combined hyperlipidemia | 238040008 |
| Fredrickson type IIb hyperlipoproteinemia | 238040008 |
| HLD—Hyperlipidemia | 55822004 |
| Hyperalphalipoproteinemia | 238080004 |
| Hyperapobetalipoproteinemia | 238040008 |
| Hyperlipidemia | 55822004 |
| Lipidemia | 55822004 |

Using the above-described algorithm(s), a lexical match is identified as "hyperlipidemia." An exemplary approach to identifying the lexical match may be to use the n-gram algorithm and n-grams with length of 3. The source may be broken down as follows:

Hyperlipemia→ 'hy', 'hyp', 'ype', 'per', 'erl', 'rli', 'lip', 'ipe', 'pem', 'emi', 'mia', 'ia'

This is a total of 12 n-grams.
The target match may be broken down into n-grams as follows:

Hyperlipidemia --? 'hy', 'hyp', 'ype', 'per', 'erl', 'rli', 'lip', 'ipi', 'pid', 'ide', 'dem', 'emi', 'mia', 'ia'

This is a total of 14 n-grams, 10 of which are the same as the source. A distance is calculated using the following Equation:

$$1-(\text{Common n-grams})/(\text{Total unique n-grams}) \quad \text{Equation 2:}$$

In the above example, the equation would appear as follows:

$$1-10/16=0.375.$$

This would be an appropriate lexical match for any situation where a distance threshold is set at any value higher than 0.375 (e.g., distance threshold up to 0.4). The distance threshold may be used to identify a match when several potential matches have a distance value.

Figure 4:
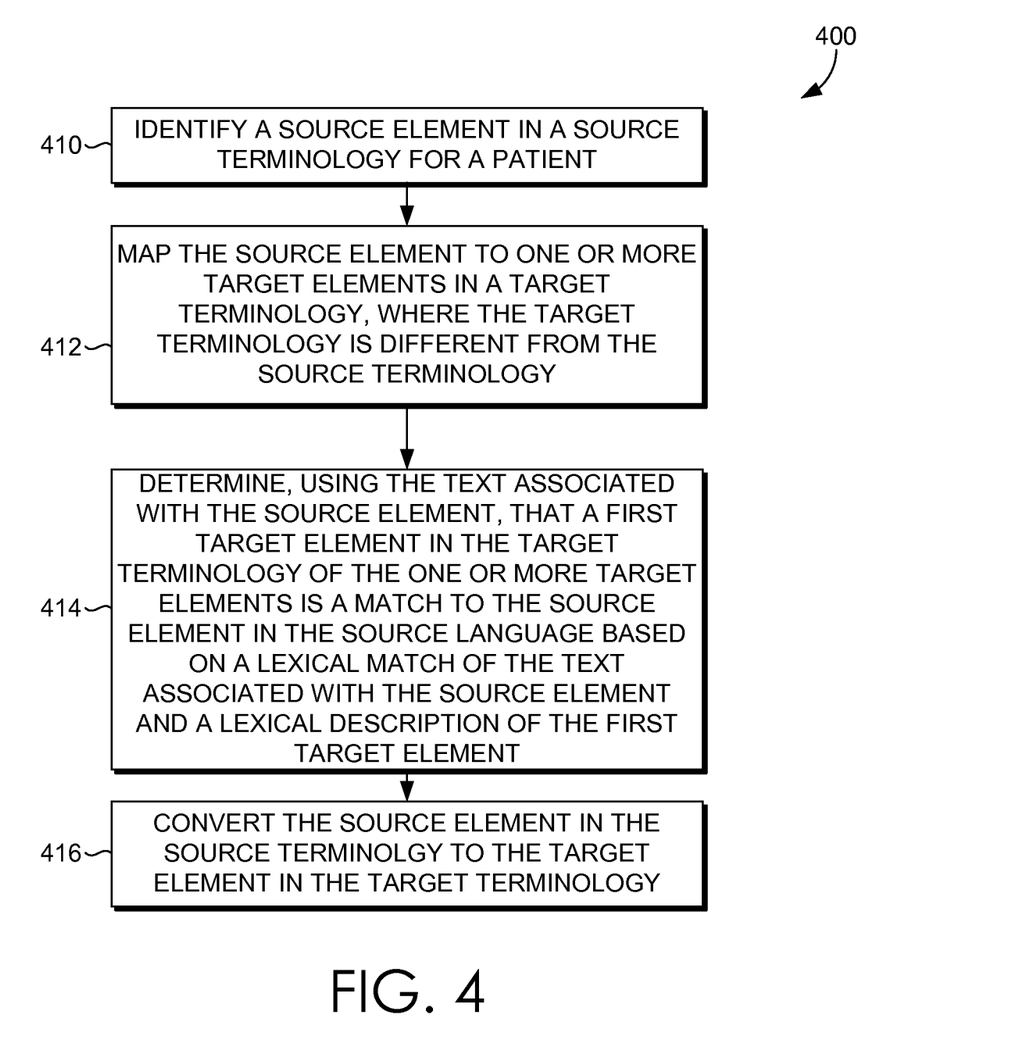
FIG. 4 depicts a flow diagram of another method for converting terms, in accordance with an embodiment of the present invention.

Turning now to FIG. 4, a flow diagram of method 400 for converting terms is provided, in accordance with an embodiment of the present invention. This is just one example and is not intended to limit the scope of other aspects described herein. At block 410, a source element in a source terminology is identified for a patient. The source element may be identified in the patient's EHR. At block 412, the source element is mapped to one or more target elements in a target terminology, where the target terminology is different from the source terminology. Mapping to one or more target elements may be achieved utilizing existing cross maps for two terminologies (if available). At block 414, it is determined, using text associated with the source element, that a first target code in the target terminology of the one or more target elements is a match to the source element in the source terminology based on a lexical match of the text associated with the source element and a lexical description of the first target element. At block 416, the source element in the source terminology is converted to the target element in the target terminology.

Figure 5:
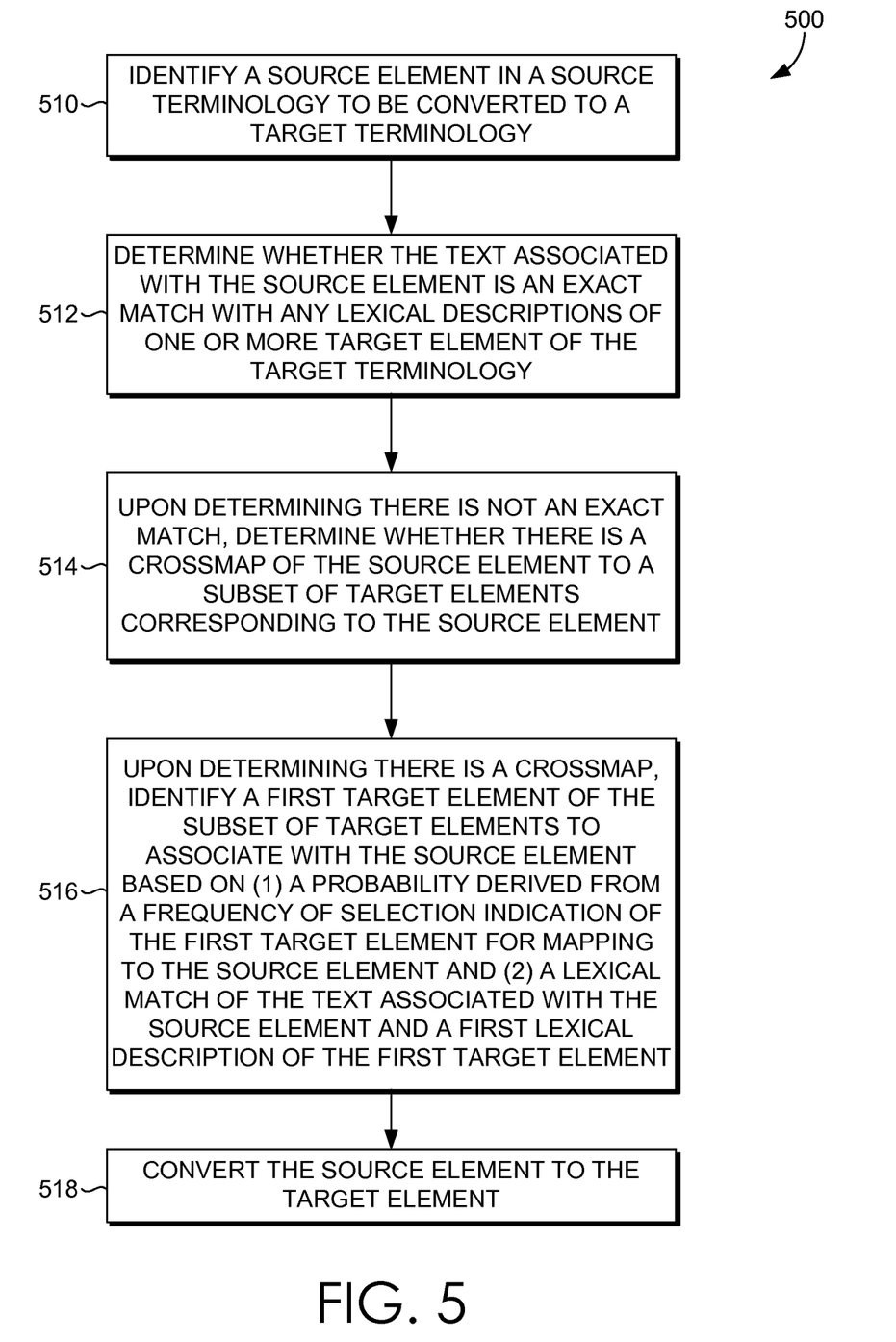
FIG. 5 depicts a flow diagram of an exemplary algorithm for carrying out embodiments of the present invention.

FIG. 5 provides a flow diagram of another method 500 for converting terms, in accordance with an embodiment of the invention. At block 510, a source element in a source terminology to be converted to a target terminology is identified. At block 512, it is determined whether text associated with the source element is an exact match with any lexical descriptions of one or more target elements of the target terminology. At block 514, upon determining there is not an exact match, it is determined whether there is a crossmap of the source element to a subset of target elements corresponding to the source element. At block 516, upon determining there is a crossmap, a first target element of the subset of target elements is identified to associate with the source element based on (1) a probability derived from a frequency of selection indication of the first target element for mapping to the source element and (2) a lexical match of the text associated with the source element and a first lexical description of the first target element. At block 518, the source element is converted to the target element. Converting a source to a target may include converting a numerical medical code value associated with a source to a numerical medical code value associated with a target and converting text associated with a source to a lexical description associated with a target.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computerized method, carried out by at least one server having one or more processors in a medical information computing system, for improving the conversion of terms by the server from a source terminology to terms of a target terminology, the method comprising:
    operating the medical information computing system with the at least one server, a database cluster, and one or more remote computers located in a medical or research environment;
    identifying, by the at least one server, a source element in the source terminology for a patient in a patient's electronic health record in the medical information computing system, wherein the source element includes a numerical medical code and a text associated therewith;
    mapping, by the at least one server, the source element to one or more target elements in the target terminology, wherein the target terminology is different from the source terminology, and wherein the one or more target elements include numerical medical codes and lexical descriptions associated therewith;
    generating a highest probability of a frequency of selection indication in the at least one server, wherein generating the highest probability comprises indicating how often a selected target element is selected at a location with respect to the source element;
    determining, by the at least one server using the text associated with the source element, that a first target element in the target terminology of the one or more target elements is a match to the source element in the source terminology, wherein the match is based on the highest probability, and wherein the source terminology is at least ICD-9 or SNOMED CT®;
    converting, by the at least one server, the source element in the source terminology to the target element in the target terminology by replacing the source element with the target element; and
    storing, by the at least one server, the target element in the patient's electronic health record in a database that is communicatively coupled to the at least one server in the medical information computing system as a specific best match in the target terminology for the source element in the source terminology.

2. The method of claim 1, wherein the source element is identified as it is input into a patient's electronic health record.

3. The method of claim 1, wherein the source element is historical input identified subsequent to being input into a patient's electronic health record.

4. The method of claim 1, wherein the text is free text manually input by a clinician while entering the source element.

5. The method of claim 1, wherein the text is text selected by a clinician from a one or more predetermined selection options while entering the source element.

6. The method of claim 1, wherein the target terminology is SNOMED CT® except when the source terminology is SNOMED CT®.

7. The method of claim 1, wherein the source terminology is ICD-9 except when the source terminology is ICD-9.

8. A system for converting terms, the system comprising:
    a conversion engine embodied on a server having one or more processors and one or more computer storage media performing an improved method of converting terms from a source terminology to a target terminology; and
    a data store coupled to the conversion engine, wherein the conversion engine:
        identifies a source element in a patient's electronic health record to be converted to a target element, each of the source element and the target element being associated with different terminologies, wherein the different terminologies are at least ICD-9 or SNOMED CT®, and wherein the source element is associated with both a first numerical medical code and a text and the target element is associated with a second numerical medical code and a lexical description;
        generates one or more of a probability derived from a frequency of selection indication of the target element at a location;
        determines a match from the one or more of the probability of the target element to the source element when mapping the source element or when mapping a lexical match of the lexical description of the target element to the text associated with the source element; and
        stores the target element in the patient's electronic health record in the data store,
        wherein the server and the data store are connected in a computing network to one or more remote computers.

9. The system of claim 8, wherein the source element is identified from a patient's electronic health record.

10. The system of claim 8, wherein the frequency of selection indication indicates how often a selected target element is selected with respect to the source element.

11. The system of claim 8, wherein the text is free text manually input by a clinician while entering the source element or the text is text selected by a clinician from a one or more predetermined selection options while entering the source element.

12. The system of claim 8, wherein a terminology associated with the target element is SNOMED CT®.

13. The system of claim 8, wherein a terminology associated with the source element is ICD-9.

14. The system of claim 8, wherein the frequency of selection indication indicates the frequency of selection within a healthcare institution.

15. One or more computer storage media having computer-executable instructions embodied thereon that, when executed, facilitate an improved method by a server of converting terms from a source terminology to a target terminology, the method comprising:
    identifying, by the server, a source element in the source terminology to be converted to the target terminology, wherein the source element includes a numerical medical code value and text associated therewith, and wherein the soure terminology is at least ICD-9 or SNOMED CT®;
    determining, by the server, whether the text associated with the source element is an exact match with any lexical descriptions of one or more target elements of the target terminology;
    upon determining there is not an exact match, the server determining whether there is a crossmap of the source element to a subset of target elements corresponding to the source element;
    upon determining there is a crossmap, generating, by the server, (1) a probability derived from a frequency of selection indication of the first target element at a location for mapping to the source element and (2) a lexical match of the text associated with the source element and a first lexical description of the first target element;

identifying, by the server, a first target element of the subset of target elements to associate with the source element;

converting, by the server, the source element to the target element, wherein the converting includes converting the text associated with the source element to the first lexical description associated with the first target element; and storing, by the server, the target element in a patient's electronic health record in a database communicatively coupled to the server.

16. The media of claim 15, wherein the source element is identified in a patient's electronic medical record.

17. The media of claim 15, wherein the crossmap is a set of mappings for elements in a first terminology to elements in a second terminology.

18. The media of claim 15, wherein the text is free text manually input by a clinician while entering the source element.

19. The media of claim 15, wherein the text is text selected by a clinician from one or more predetermined selection options while entering the source element.

20. The method of claim 1, wherein the frequency of selection indication is derived from data specific to a particular institution, to a specific department within an organization, or to a geographic region smaller than an entire country.

* * * * *

UNITED STATES PATENT AND TRADEMARK OFFICE
CERTIFICATE OF CORRECTION

PATENT NO. : 10,741,272 B2  
APPLICATION NO. : 14/521557  
DATED : August 11, 2020  
INVENTOR(S) : Savitha Venkat et al.

Page 1 of 1

It is certified that error appears in the above-identified patent and that said Letters Patent is hereby corrected as shown below:

In the Specification

Column 09, Line 59: Please remove "Equation 1" and replace with --Equation 1:--.

In the Claims

Column 16, Line 54: Please remove "soure" and replace with --source--.

Signed and Sealed this  
Twenty-second Day of September, 2020

Andrei Iancu  
*Director of the United States Patent and Trademark Office*